United States Patent
Jaeger et al.

(10) Patent No.: US 7,893,262 B2
(45) Date of Patent: Feb. 22, 2011

(54) PROCESS FOR THE PREPARATION OF 2H-CHROMENES

(75) Inventors: Jurgen Jaeger, Reinach (CH); Kaspar Burri, Binningen (CH); Sorana Greiveldinger-Poenaru, Rheinfelden (CH); Johannes Hoffner, Ziefen (CH)

(73) Assignee: Arpida AG, Muenchenstein (CH)

( * ) Notice: Subject to any disclaimer, the term of this patent is extended or adjusted under 35 U.S.C. 154(b) by 958 days.

(21) Appl. No.: 10/567,558

(22) PCT Filed: Aug. 3, 2004

(86) PCT No.: PCT/EP2004/008682

§ 371 (c)(1),
(2), (4) Date: Apr. 6, 2007

(87) PCT Pub. No.: WO2005/014587

PCT Pub. Date: Feb. 17, 2005

(65) Prior Publication Data

US 2008/0015354 A1    Jan. 17, 2008

(30) Foreign Application Priority Data

Aug. 8, 2003    (WO) ............... PCT/EP03/08814

(51) Int. Cl.
*C07D 405/06* (2006.01)
*C07D 311/58* (2006.01)

(52) U.S. Cl. .............. 544/323; 544/324; 549/405; 549/406

(58) Field of Classification Search .......... 544/323, 544/324; 514/405; 549/405, 406
See application file for complete search history.

(56) References Cited

U.S. PATENT DOCUMENTS

| 5,502,220 A | 3/1996 | North |
| 5,773,446 A | 6/1998 | Masciadri |

FOREIGN PATENT DOCUMENTS

| CN | 1203600 A | 12/1998 |
| EP | 0 629 619 A1 | 12/1994 |
| HU | P 93 00120 | 12/1993 |
| JP | 07-053541 A | 2/1995 |
| WO | WO-97/20839 A1 | 6/1997 |
| WO | WO-03/051863 A1 | 6/2003 |
| WO | WO-2005/014587 | 2/2005 |

OTHER PUBLICATIONS

International Search Report dated Nov. 16, 2004.
Novelty Search Report issued from Hungarian Patent Office, corresponding to Hungary patent application P 06 00231, dated Jan. 23, 2008.
*A Course in Experimental Chemistry*, vol. 20, Organic Synthesis II, Alcohols and Amines, pp. 10-14, 1992, edited by The Chemical Society of Japan and published by Maruzen; (English translation of Reduction of carboxylic acids attached).
Sylvain Gauthier, et al.; "(S)-(+)-4-[7-(2,2-Dimethyl-1-oxopropoxy)-4-methyl-2-[4-[2-(1-piperidinyl)-ethoxy]phenyl]-2H-1-benzopyran-3yl]-phenyl 2,2-Dimethylpropanoate (EM-800): A Highly Potent, Specific, and Orally Active Nonsteroidal Antiestrogen"; Journal of Medical Chemistry, 1997, vol. 40, No. 14, pp. 2117-2122.
Japanese Office Action issued for JP Appl No. 2006-522311, with English translation, dated Aug. 22, 2010 (relates to citations BA and CA).

*Primary Examiner*—Deepak Rao
(74) *Attorney, Agent, or Firm*—Dickstein Shapiro LLP

(57) ABSTRACT

The invention concerns a novel process for the preparation of 2H-chromenes of formula I and formula 5 and valuable intermediates of formulae 3 and 4 of this process.

5 Claims, No Drawings

PROCESS FOR THE PREPARATION OF 2H-CHROMENES

This application is a 371 of PCT/EP04/08682 filed Aug. 3, 2004.

FIELD OF THE INVENTION

The present invention relates to a novel processes for the preparation of 2H-chromenes especially of the compound of formula I (Iclaprim)

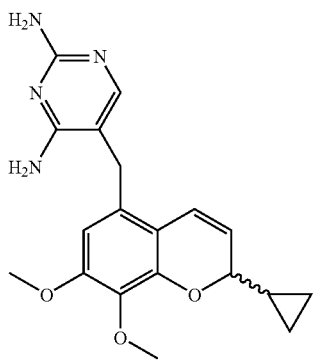

and to valuable intermediates of this process.

BACKGROUND OF THE INVENTION

The compound of formula I has valuable antibiotic properties. The compound can be used in the control or prevention of infectious diseases in mammals, both humans and non-humans. In particular, it exhibits a broad spectrum of antimicrobial activity including multi-drug resistant pathogens. The compound can also be administered in combination with known substances of antibacterial activity and exhibits synergistic effects with some of them.

Typical combination partners are e.g. sulfonamides or other inhibitors of enzymes which are involved in folic acid biosynthesis such as, for example, pteridine derivatives.

A current method of preparing compound I is described in the U.S. Pat. No. 5,773,446. The drawback of this synthesis is the lengthy synthesis and consequently the low overall yield. Most of the intermediates are not crystalline, which renders this synthesis economically less attractive as an industrial process. In addition, some expensive reagents cannot be recovered.

This problem is further complicated by the use of halogenated solvents, e.g. methylene chloride. Halogenated solvents are expensive to handle and to dispose properly, thus leading to an added cost.

Therefore, there is a need for a process for preparing the compound of formula I with a higher overall yield and a reduced number of reaction product isolation steps. There is also a need for a process where all isolated intermediates are crystalline and do not require chromatography.

SUMMARY OF THE INVENTION

The present invention provides a process for preparing the compound of the formula I

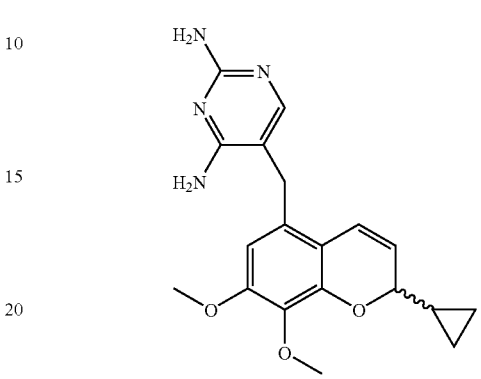

by reacting either a compound of formula 1 (compare Scheme 1 below) with a compound of formula 9 to obtain a compound of formula 2, which is hydrolyzed to a compound of formula 3, which in turn is reduced to a compound of formula 4, or reducing the compound of formula 2 directly to the compound of formula 4, and thereafter oxidizing the compound of formula 4 to obtain the compound of formula 5, or reacting a compound of formula 6 with a compound of formula 9 to obtain the compound of formula 5.

The compound of formula 5 as prepared according to the forgoing reaction steps is the central intermediate in the preparation of the compound of formula I. It may be mentioned that the compounds of formulae 2 and 5 need not to be isolated. It appears also to be surprising that the common reactant, i.e. the compound of formula 9, can be reacted with either the compound of formula 1 or the compound of formula 6 in an alkaline reaction medium in which neither the ester 1 nor the aldehyde 6 is expected to be stable.

Compound of formula 5 is transformed into the compound of formula I by reacting the compound of formula 5 with a compound of formula 10 to obtain the compound of formula 11 which in turn can be transformed into the compound of formula I (Scheme 3).

The preparation of the central intermediate of formula 5 is depicted in Scheme 1 and the common intermediate 9 is synthesized from the commercially available compound 7 as depicted in Scheme 2.

The compound of formula I is basic in nature and can be, if desired, transformed with an acid into a pharmaceutically acceptable acid addition salt. Suitable acids are, e.g. hydrochloric acid, maleic acid, methane sulfonic acid and lactic acid. Most preferred is methane sulfonic acid.

In the synthesis the racemate of the compound of formula I is obtained. However and if desired, the racemate may be resolved in a manner known per se, e.g. by crystallization in the presence of an optically active acid or by chromatography.

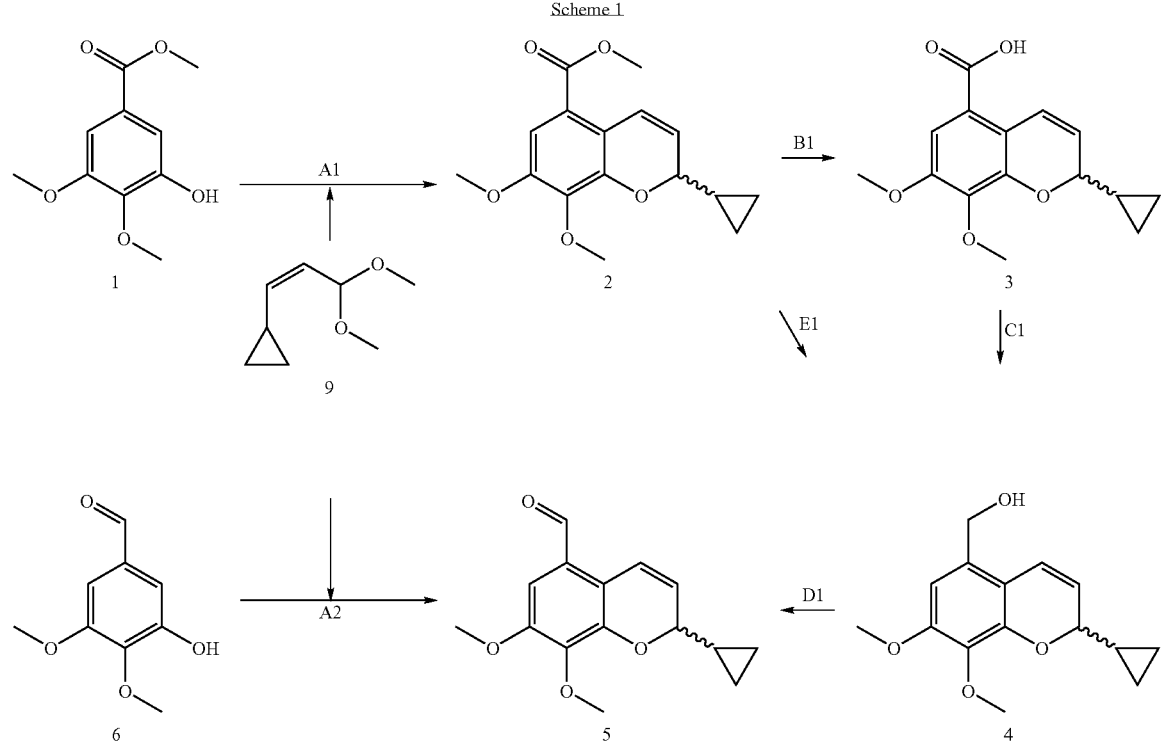
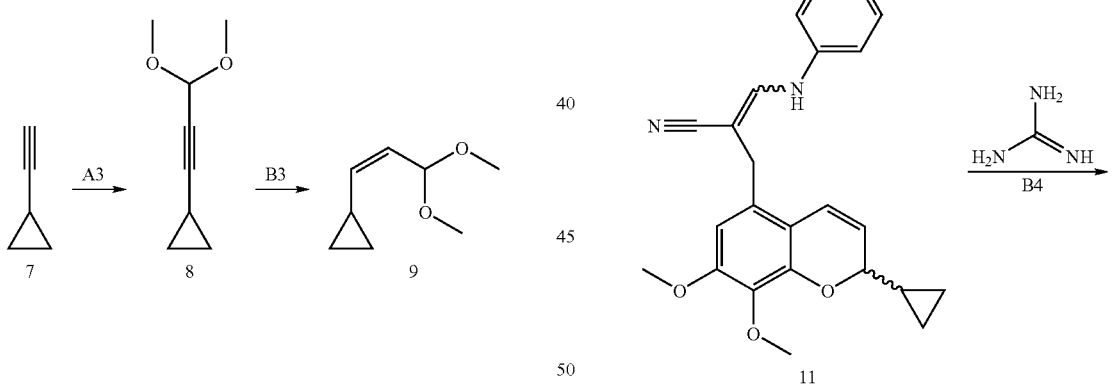
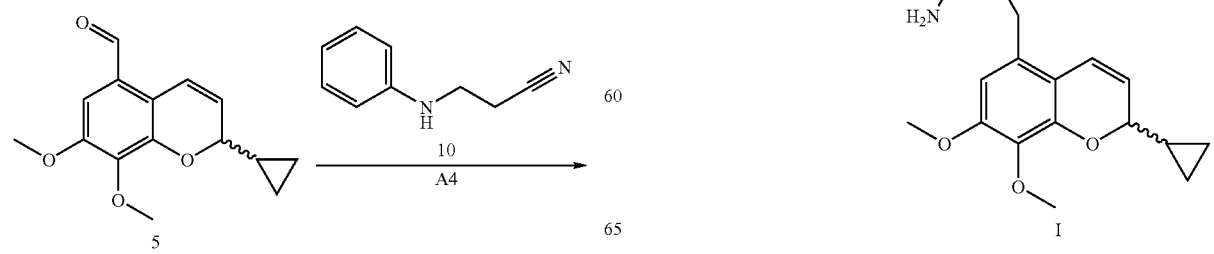

DETAILED DESCRIPTION OF THE INVENTION

The process of the present invention provides many advantages and improvements over the current process of synthesizing the above aldehyde of formula 5 and subsequently Iclaprim of formula I. The corresponding starting materials of formulae 1, 6 and 7 are commercially available in bulk quantities.

In order to prepare the compound of formula I the central intermediate of formula 5 may be prepared following the reaction sequence A1, B1, C1 and D1. The cyclisation A1 can be done by heating a compound of formula 1 with a compound of formula 9 in an inert, high boiling solvent like toluene, p-xylene and in the presence of a base, like 3-picoline, N,N; N',N'-tetramethylethylenediamine up to about 100°-170° C. The saponification B1 of the ester 2 can be effected in alcohols, e.g. methanol, isopropanol or a mixture of acetone and isopropanol at room temperature or up to 60° C. with alkali hydroxides, e.g. sodium or potassium hydroxide. The reduction C1 of compound 3 is preferably carried out at room temperature or a slightly elevated temperature up to 50° C. in an inert solvent, e.g. tert. butylmethyl ether (TBME), tetrahydrofurane, toluene or a mixture of toluene and TBME with, e.g. lithium aluminium hydride, sodium dihydrido-bis(2-methoxy-ethoxy)aluminate (Red-AL). Compound 5 can also be obtained from 2 through reduction E1 in an inert solvent, e.g. tert. butylmethyl ether (TBME), tetrahydrofurane, toluene or a mixture of toluene and TBME with, e.g. lithium aluminium hydride, sodium dihydrido-bis (2-methoxy-ethoxy)aluminate (Red-AL) at room temperature up to 50° C. The oxidation D1 of compound 4 can be done, e.g. in dimethyl sulfoxide with sulfur trioxide pyridine complex and triethylamine at 0°-20° C.

The compound of formula 5 can also be produced with the reaction sequence as depicted in Scheme 1. The cyclisation A2 can be done by heating a compound of formula 6 with a compound of formula 9 in an inert, high boiling solvent like toluene, p-xylene and in the presence of a base, like 3-picoline, N,N; N',N'-tetramethylethylenediamine up to about 100°-170° C. The reaction of aldehyde 6 under basic condition at elevated temperature is rather unexpected due to the propensity of aldehydes to polymerize under similar conditions.

The production of the compound of formula 9 as depicted in Scheme 2 can be performed in accordance with the reaction sequence A3 and B3. The intermediate magnesium bromide salt of cyclopropyl acetylene (compound 7) is produced in an inert solvent, e.g. tetrahydrofurane or toluene by adding a lower alkyl magnesium bromide, e.g. ethyl, butyl or cyclohexyl at 30°-80° C. The condensation of the anion of compound 7 with a trialkyl-orthoformiat, e.g. trimethyl-orthoformiate or triethyl-orthoformiate takes place at 50°-120° C. by slowly distilling off the solvent. The hydrogenation of compound 8 according to step B3 can be carried out, e.g. by reaction of compound 8 in an inert solvent like ethyl acetate in the presence of a Lindlar catalyst which is poisoned with e.g. 3,6-dithia-1,8-octanediol at room temperature or at elevated temperature up to 60° C. and 1-5 bar hydrogen pressure.

The compounds of formulae 3 and 4 are novel and are also objects of the invention. They can be prepared according to the reaction sequences elucidated in Scheme 1. The preparation of compounds outlined in Schemes 1, 2 and 3 is, moreover, described in more detail in the examples.

As already mentioned, the compound of formula I or their pharmaceutical acceptable salts have valuable antibacterial properties. This compound is active against a large number of pathogenic microorganisms such as e.g. *S. aureus, P. carinii* etc. by virtue of their activity in inhibiting bacterial dihydrofolate reductase (DHFR). The activity of this compound is described in more detail in P. G. Hartmann et al. *Abstracts*, F2020, 42nd Interscience Conference on Antimicrobial Agents and Chemotherapy, San Diego, Calif., Sep. 27-30, 2002; American Society for Microbiology: Washington, D.C., 2002.

Additional objects, advantages, and novel features of this invention will become apparent to those skilled in the art upon examination of the following examples, which are not intended to be limiting the scope of the invention.

The following examples illustrate the invention in more detail. Examples 1 to 7 describe the preparation of compound 5, while example 8 and 9 describe the preparation of the compound of formula 9, and examples 10 and 11 describe the transformation of the compound of formula 5 to the endproduct of formula I (Iclaprim). The temperatures are given in degrees Celsius.

EXAMPLES

The compound of formula 1 can be synthesized e.g. according M. Tanaka et al., Tetrahedron, 51, 11703 (1995). Compound of formula 6 can be produced e.g. according A. K. Sinhababu et al., J. Org. Chem., 48, 1941-1944 (1983). Compound 7 can be prepared e.g. according S. E. Schmidt et al., Synlett, 12, 1948-1950 (1999).

All other reagents and solvents are readily commercially available, for example from Fluka or equivalent commercial suppliers.

| | |
|---|---|
| TBME | Tert•Butyl methyl ether |
| IPAc | Isopropylacetate |
| DMSO | Dimethyl sulfoxide |
| RT | Room temperature |
| Red-Al | Dihydrido-bis(2-methoxy-ethoxy)aluminate |
| THF | Tetrahydrofurane |

Example 1

This example illustrates the preparation of 2-cyclopropyl-7,8-dimethoxy-2H-chromene-5-carboxylic acid methyl ester 2 (step A1).

3-Hydroxy-4,5-dimethoxy-benzoic acid methyl ester 1 (20 g, 94 mmol) and cis-(3,3-dimethoxy-propenyl)-cyclopropane 9 (22.3 g, 90% pure, 141 mmol) were dissolved in 70 ml p-xylene and 3-picoline (3.6 ml, 37.6 mmol) were added. The mixture was heated up to reflux (oil-bath 160° C.) and the formed methanol was removed by a distillation head. A heated reflux condenser at 70° C. between reaction vessel and distillation head was used to specifically remove the formed methanol. After 24 hours the reaction mixture was worked up simply by distilling off the xylene and unreacted acetal. The dark oil was used directly in the next step.

Isolation of 2 is possible by crystallizing e.g. 2.6 g 2 from methylcyclohexane/TBME (3:1, 10 ml) after cooling (−20° C. 18 h). 1.07 g of pure 2 was isolated as a white-yellow solid.

$^1$H-NMR (CDCl$_3$) δ(ppm): 7.25 (dd, 1H, J$_1$=10.1 Hz, J$_2$=1.5 Hz); 7.09 (s, 1H, C6H); 5.8 (dd, 1H, J$_1$=10.1 Hz, J$_2$=4.0 Hz); 4.24 (ddd, 1H, J$_1$=8.6 Hz, J$_2$=4.0 Hz, J$_3$=1.5 Hz);

3.95 (s, 3H, OCH$_3$); 3.88 (s, 6H, 2×OCH$_3$); 1.2-1.3 (m, 1H,), 0.32-0.62 (m, 4H); mp.: 61° C.

Example 2

This example illustrates the preparation of 2-cyclopropyl-7,8-dimethoxy-2H-chromene-5-carboxylic acid 3 (step B1).

Crude 2 (14.1 g, 60% content, 29.2 mmol) was dissolved in 135 ml of isopropanol/acetone (5:1) and 29 ml 4N NaOH solution was added. The reaction mixture was stirred 30 minutes at room temperature 1 h at 50° C. The solvents were then evaporated and the residue dissolved with 100 ml water and treated with charcoal to remove impurities and polymeric products. After filtration the aqueous layer was extracted with 2 times 100 ml TBME. Isopropyl acetate was added to the aqueous phase. The pH of the solution was adjusted to pH=1 with concentrated HCl. After separation, the aqueous phase was extracted with 2 times 100 ml of IPAc and the combined organic phase concentrated to dryness. The oil was crystallized from IPAc/heptane. Compound of formula 3 (7.8 g) was isolated as light brown crystals.

$^1$H-NMR (CDCl$_3$) δ(ppm): 7.44 (dd, 1H, J$_1$=10.36 Hz, J$_2$=1.52 Hz); 7.23 (d, 1H); 5.86 (dd, 1H, J$_1$=10.36 Hz, J$_2$=3.8 Hz); 4.26 (ddd, 1H, J$_1$=8.32 Hz, J$_2$=3.8 Hz, J$_3$=1.76 Hz); 3.98 (s, 3H, OCH$_3$); 3.9 (s, 3H, OCH$_3$); 1.33-1.23 (m, 1H, CH), 0.33-0.64 (m, 4H); mp.: 124-126.5° C.

Example 3

This example illustrates the preparation of (2-cyclopropyl-7,8-dimethoxy-2H-chromen-5-yl)-methanol 4 (step C1).

To a solution of the acid 3 (7.8 g, 28.2 mmol) in dry THF (150 ml) LiAlH$_4$ (0.85 g, 0.8 eq, 22.6 mmol) was added at 15° C. under Argon. Then the mixture was allowed to warm to RT and then stirred for 1 h at 50° C.

The quenching and work up was done adding 0.85 ml water and 0.85 g NaOH in 2.5 ml water. The precipitated aluminate salts were filtered and the organic phase was concentrated to dryness. Crude compound 4 was obtained as a light brown solid (usually in quantitative yield), which was further used as such.

A sample was crystallized from methylcyclohexane/TBME (1:1) providing material for the NMR:

$^1$H-NMR (CDCl$_3$) δ(ppm): 6.65 (d, 1H, J=10.1 Hz), 6.48 (s, 1H); 5.73 (dd, 1H, J$_1$=10.1 Hz, J$_2$=4 Hz); 4.64 (s, 2H); 4.2-4.26 (m, 1H); 3.88 (s, 3H, CH$_3$); 3.84 (s, 3H, CH$_3$); 1.73 (bs, 1H, OH); 1.21-1.31 (m, 1H, CH), 0.31-0.61 (m, 4H); mp.: 94-96° C.

Example 4

This example illustrates the preparation of (2-cyclopropyl-7,8-dimethoxy-2H-chromen-5-yl)-methanol 4 (step C1).

The acid 3 (5.7 g, 20.7 mmol) was dissolved in dry TBME/toluene (1:1, 100 ml) and a solution of Red-Al (9.2 ml, 3.5-M in toluene, 32.1 mmol) in 15 ml toluene was added over a period of 20 minutes. During the addition the temperature was kept at 30° C. The reaction mixture was stirred for 90 minutes at 50° C. and then poured over ice-water and acidified with 2.5-N sulfuric acid. After extraction of the product with TBME, the organic layer was washed with brine, 0.1-N NaOH and again with brine. After drying over magnesium sulfate and evaporation of the solvent 4 (4.8 g, 18.3 mmol) was obtained as a yellow-white solid.

A sample was crystallized from methylcyclohexane/TBME (1:1) providing material for the NMR:

$^1$H-NMR (CDCl$_3$) δ(ppm): 6.65 (d, 1H, J=10.1 Hz), 6.48 (s, 1H, C6H); 5.73 (dd, 1H, J$_1$=10.1 Hz, J$_2$=4 Hz); 4.64 (s, 2H, CH$_2$); 4.2-4.26 (m, 1H); 3.88 (s, 3H, CH$_3$); 3.84 (s, 3H, CH$_3$); 1.73 (bs, 1H, OH); 1.21-1.31 (m, 1H, CH), 0.31-0.61 (m, 4H); mp.: 94-96° C.

Example 5

This example illustrates the preparation of (2-cyclopropyl-7,8-dimethoxy-2H-chromen-5-yl)-methanol 4 (step E1).

Methyl ester 2 (2 g, 6.2 mmol) was dissolved in 30 ml tetrahydrofurane and 2.7 ml of a 3.5-M solution of Red-Al (9.4 mmol) was added. The mixture was stirred at 40° C. for 3 hours. The solution was diluted with 100 ml of TBME and slowly quenched by addition of 50 ml of a 30% potassium-tartrate solution. The layers were separated and the organic solution was washed with brine (2 times 30 ml), dried over magnesium sulfate and concentrated. The pure alcohol 4 (1.34 g, 5.1 mmol) was obtained as a white-yellow solid.

A sample was crystallized from methylcyclohexane/TBME (1:1) providing material for the NMR:

$^1$H-NMR (CDCl$_3$) δ(ppm): 6.65 (d, 1H, J=10.1 Hz), 6.48 (s, 1H); 5.73 (dd, 1H, J$_1$=10.1 Hz, J$_2$=4 Hz); 4.64 (s, 2H, CH$_2$); 4.2-4.26 (m, 1H); 3.88 (s, 3H, CH$_3$); 3.84 (s, 3H, CH$_3$); 1.73 (bs, 1H, OH); 1.21-1.31 (m, 1H, CH), 0.31-0.61 (m, 4H); mp.: 94-96° C.

Example 6

This example illustrates the preparation of 2-cyclopropyl-7,8-dimethoxy-2H-chromene-5-carbaldehyde 5 (step D1).

A solution of sulfur trioxide-pyridine complex (17 g, 107 mmol), 7.5 ml DMSO and 17 ml triethylamine in 20 ml toluene is cooled to 10° C. A solution of 4 (11.2 g, 42.7 mmol) in 15 ml toluene is then slowly, added. After 5 h stirring at 20° C., then 40 ml water were added and the reaction mixture was stirred overnight at RT. The aqueous phase was extracted with toluene (3 times 20 ml) and the combined organic phases were concentrated to dryness. A brown-orange oil was obtained in quantitative yield and used in the next step.

A sample was crystallized from methylcyclohexane/TBME (1:1) providing material for the NMR:

$^1$H-NMR (CDCl$_3$) δ(ppm): 10.11 (s, 1H, CHO); 7.31 (d, 1H, J=10.1 Hz); 6.9 (s, 1H); 5.91 (dd, 1H, J$_1$=10.1, J$_2$=3.5 Hz); 4.24-4.29 (m, 1H); 3.98 (s, 3H, OCH$_3$); 3.9 (s, 3H, OCH$_3$); 1.21-1.31 (m, 1H, CH); 0.32-0.62 (m, 4H); mp: 44-47° C.

Example 7

This example illustrates the preparation of 2-cyclopropyl-7,8-dimethoxy-2H-chromene-5-carbaldehyde 5 (step A2).

Compound 6 (5 g, 27.4 mmol) and cis-(3,3-dimethoxy-propenyl)-cyclopropane 9 (7.6 g, 90% pure, 48 mmol) were dissolved in 33 ml p-xylene and 3-picoline (0.64 g, 6.8 mmol) was added. The mixture was heated up under argon atmosphere to reflux (oil-bath 160° C.) and the generated methanol was removed by a distillation head. A heated reflux condenser at 75° C. between reaction vessel and distillation head was used to specifically remove the methanol only. After 25 hours the reaction mixture was cooled down to RT and ethyl acetate (400 ml) was added. The mixture was then washed with 0.1-N HCl (2 times 50 ml) solution and with 1-N NaOH solution (2 times 50 ml). The organic solution was then dried over magnesium sulfate and concentrated under reduced pressure. A dark brown oil (7.9 g) was obtained. The oil was then distilled (Kugelrohr-apparatus) to obtain 4.8 g (80% purity, 14.7 mmol) of a yellow oil (bp 220-240° C., 0.5 mmbar).

$^1$H-NMR (CDCl$_3$) δ(ppm): 10.11 (s, 1H, CHO); 7.31 (d, 1H, J=10.1 Hz); 6.9 (s, 1H); 5.91 (dd, 1H, J$_1$=10.1, J$_2$=3.5 Hz); 4.24-4.29 (m, 1H); 3.98 (s, 3H, OCH$_3$); 3.9 (s, 3H, OCH$_3$); 1.21-1.31 (m, 1H, CH); 0.32-0.62 (m, 4H).

Example 8

This example illustrates the preparation of (3,3-dimethoxy-prop-1-ynyl)-cyclopropane 8 (step A3).

Magnesium (26.7 g, 1.1 mol) was suspended in 350 ml tetrahydrofurane and ethylbromide (74.6 ml, 1 mol) was added at such a rate, that the tetrahydrofurane continued to reflux. After completion of the addition the mixture was stirred one hour at 50-60° C. to complete the reaction. After cooling to room temperature ethynyl-cyclopropane 7 (80.6 ml, 70% in toluene, 0.95 mol) was added slowly during 30 minutes (evolution of ethane!) to the Grignard-reagent. After the addition the mixture was stirred one more hour at RT before trimethylorthoformate (120.3 ml, 1.1 mol) and toluene (400 ml) were added. The mixture was heated up (oil-bath temperature 100°-120° C.) and the tetrahydrofurane was removed by distillation during 4 hours. After cooling to RT and stirring over night the reaction mixture was diluted by addition of TBME (500 ml) and water was slowly added (50 ml). The clear organic solution was decanted from the highly viscous magnesium hydroxide phase. The magnesium hydroxide phase was extracted two more times with TBME (2 times 100 ml) and the combined organic solutions were dried over magnesium sulfate, filtered and concentrated. Compound 8 was isolated through vacuum-distillation (10 mbar, bp: 55°-60° C., 99 g, 0.7 mol).

$^1$H-NMR (CDCl$_3$) δ(ppm): 5.09 (d, 1H, J=1.5 Hz, CH); 3.33 (s, 6H, 2×CH$_3$); 1.22-1.32 (m, 1H, CH), 0.71-0.81 (m, 4H, 2×CH$_2$).

Example 9

This example illustrates the preparation of (3,3-dimethoxy-propenyl)-cyclopropane 9 (step B3).

(3,3-Dimethoxy-prop-1-ynyl)-cyclopropane 8 (40 g, 0.28 mol) was dissolved in ethyl acetate (500 ml) and Lindlar-Catalyst (5 g, 5% Pd "Fluka") and 3 mg of 3,6-Dithia-1,8-octandiol was added. The reactor was evaporated and set under hydrogen atmosphere 3 times, then left under hydrogen pressure (~1 bar) and the suspension was vigorously stirred for about 2.5 hours until then the calculated hydrogen volume was taken up. When the starting material had disappeared, the mixture was filtered and concentrated at reduced pressure. Except for the presence of some ethyl acetate the product 9 is pure by $^1$H-NMR. It was used without further treatment for the next reaction based on a purity of 90%.

$^1$H-NMR (CDCl$_3$) δ(ppm): 5.22 (dd, 1H, J$_1$=11 Hz, J$_2$=6.5 Hz, CHCH(OCH$_3$)$_2$); 5.22 (dd, 1H, J$_1$=6.5 Hz, J$_3$=1 Hz, CHCH(OCH$_3$)$_2$); 4.98 (dd, J$_1$=11 Hz, J$_3$=1 Hz, CH); 3.35 (s, 6H, 2×OCH$_3$), 1.6-1.75 (m, 1H, CH), 0.75-0-81 (m, 2H, CH$_2$), 0.38-0.4 (m, 2H, CH$_2$).

Example 10

This example illustrates the preparation of 2-(2-cyclopropyl-7,8-dimethoxy-2H-chromen-5-ylmethyl)-3-phenylamino-acrylonitrile 11 (step A4).

Under N$_2$ at 10° C., the aldehyde 5 (3.75 g, 80% pure, 11.5 mmol) and freshly crystallized 3-anilinopropionitrile (1.9 g, 13 mmol) was dissolved in DMSO (20 ml). Potassium tert-butoxide (1.7 g, 16 mmol) was added in portions at 10° C. to the reaction mixture. After the addition the mixture was allowed to warm to room temperature and was stirred for 3 hours. The color of the solution changed from yellow to dark brown. Then 50 ml of cold water were added and the mixture was extracted with ethyl acetate (3 times 100 ml). The combined organic layers were washed with brine (2 times 100 ml) and dried over magnesium sulfate. Activated carbon was added to the solution to remove the color and the mixture was stirred for 30 minutes, then filtered. The solvent was removed to give 5.2 g of a dark brown oil which is usually further used without isolation.

Crystallization from ethanol/hexane (1:1) resulted 11 (2.2 g, 5.67 mmol), as a mixture of cis/trans isomers. The mother liquor contained some more 11.

Cis-compound: $^1$H-NMR (CDCl$_3$) δ(ppm): 7.23.7.34 (m, 3H, anilin), 6.9-7.02 (m, 1H, anilin), 6.79 (d, 2H, anilin), 6.68 (d, 1H, J=12.6 Hz, CH); 6.54 (d, 1H, J=10.1 Hz); 6.34 (s); 5.75 (dd, 1H, J$_1$=10.1 Hz, J$_2$=4 Hz); 4.23-4.27 (m, 1H); 3.9 (s, 3H, OCH$_3$); 3.85 (s, 3H, OCH$_3$); 3.47 (s, 2H, CH$_2$), 1.56 (bs, 1H, NH); 1.18-1.29 (m, 1H, CH); 0.3-0.6 (m, 4H).

Trans-compound: $^1$H-NMR (CDCl$_3$) δ(ppm): 7.23.7.34 (m, 3H, anilin), 6.9-7.02 (m, 1H, anilin), 6.74 (d, 2H, anilin); 6.60 (d, 1H, J=10.1 Hz, C4H); 6.43 (s); 6.28 (d, 1H, J=12.6 Hz, CH); 5.80 (dd, 1H, J$_1$=10.1 Hz, J$_2$=4 Hz); 4.23-4.27 (m, 1H, C2H); 3.9 (s, 3H, OCH$_3$); 3.85 (s, 3H, OCH$_3$); 3.53 (s, 2H, CH$_2$), 1.56 (bs, 1H, NH); 1.18-1.29 (m, 1H, CH); 0.3-0.6 (m, 4H).

Example 11

This example illustrates the preparation of compound of formula I (step B4). Guanidine hydrochloride (1.62 g, 17 mmol) was suspended in dry ethanol (20 ml) and potassium tert-butoxide (1.9 g, 17 mmol) was added. The mixture was stirred for 15 minutes, then filtered, the filter cake was washed once with ethanol (10 ml). The combined filtrates were added to a suspension of 11 (2.2 g, 5.67 mmol) in ethanol (20 ml) and the reaction mixture was heated up to 85° C. under argon atmosphere for 8 hours, by which time no more 11 was detected by HPLC.

The reaction mixture was concentrated to a volume of 25 ml under reduced pressure and cooled to 4° C. The crystallized I was filtered off, washed with cold ethanol and dried under vacuum (1.7 g, 4.8 mmol).

$^1$H-NMR (D$_6$-DMSO) δ(ppm): 7.07 (s, 1H, CH-pyrimidine), 6.45 (d, 1H, J=10 Hz, C4H); 6.42 (s, 1H); 6.17 (bs, 2H, NH$_2$); 5.7 (dd, 1H, J$_1$=10 Hz, J$_2$=4 Hz); 5.65 (bs, 2H, NH$_2$); 4.2-4.3 (m, 1H); 3.73 (s, 3H, OCH$_3$); 3.70 (s, 3H, OCH$_3$), 3.5 (s, 2H, CH$_2$); 1.06-1.2 (m, 1H, CH); 0.26-0.54 (m, 4H), mp.: 226-227° C.

The invention claimed is:

1. A process for preparing the compound of formula I

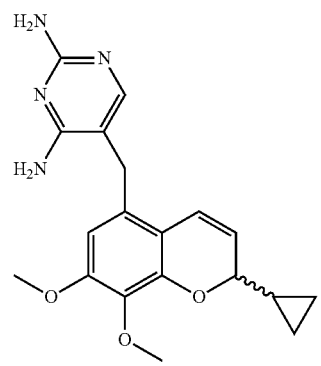

comprising:

a) reacting either a compound of formula 1 with a compound of formula 9 to obtain a compound of formula 2, which is hydrolyzed to the compound of formula 3, which in turn is reduced to a compound of formula 4 and thereafter oxidized to obtain the compound of formula 5; or c) reacting a compound of formula 6 with a compound of formula 9 to obtain the compound of formula 5; and

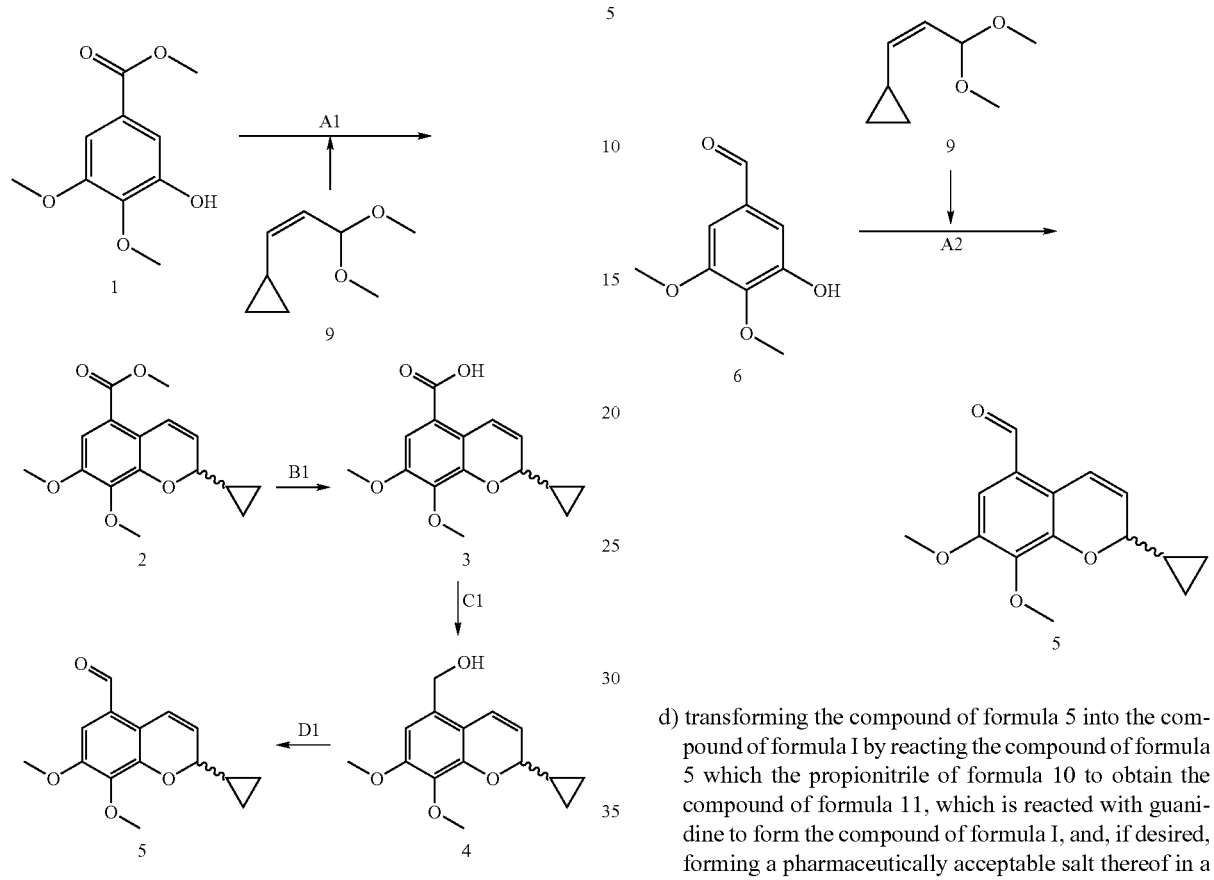

b) reducing the compound of formula 2 directly to the compound of formula 4, and thereafter oxidizing the compound of formula 4 to form the compound of formula 5; or d) transforming the compound of formula 5 into the compound of formula I by reacting the compound of formula 5 which the propionitrile of formula 10 to obtain the compound of formula 11, which is reacted with guanidine to form the compound of formula I, and, if desired, forming a pharmaceutically acceptable salt thereof in a manner known per se

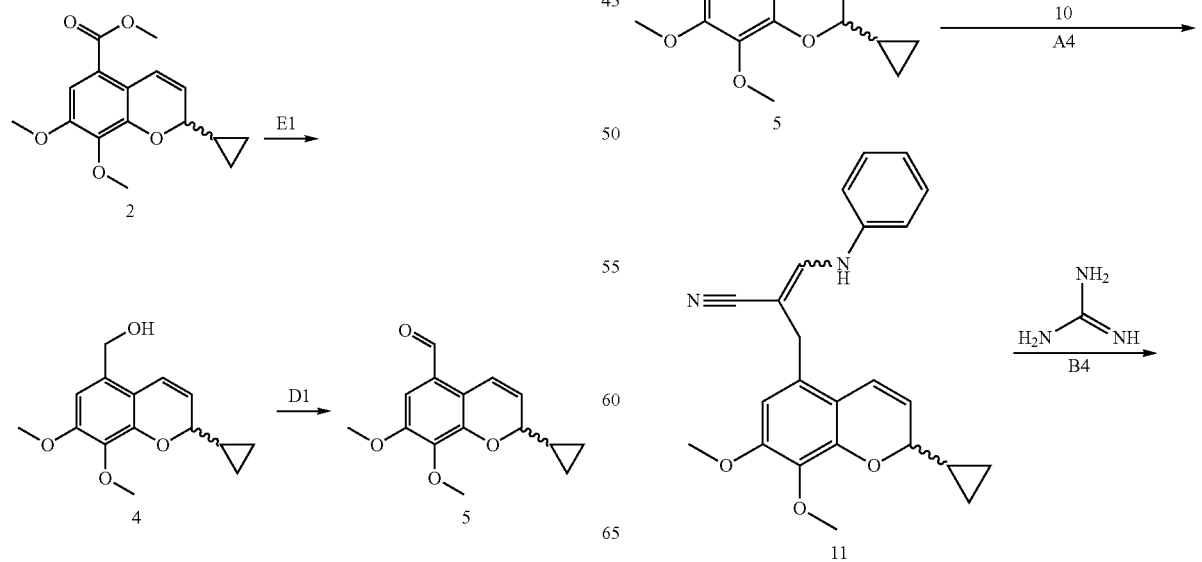

-continued

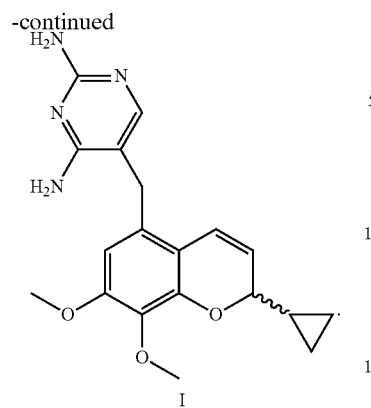

I

2. The process of claim 1, wherein the compounds of formulae 2, 5 and 11 are used in the subsequent step without isolation.

3. A process for preparing the compound of formula 5

5 comprising a) reacting a compound of formula 1 with a compound of formula 9 to obtain a compound of formula 2, which is hydrolyzed to the compound of formula 3, which is turn is reduced to a compound of formula 4 and thereafter oxidized to obtain the compound of formula 5; or

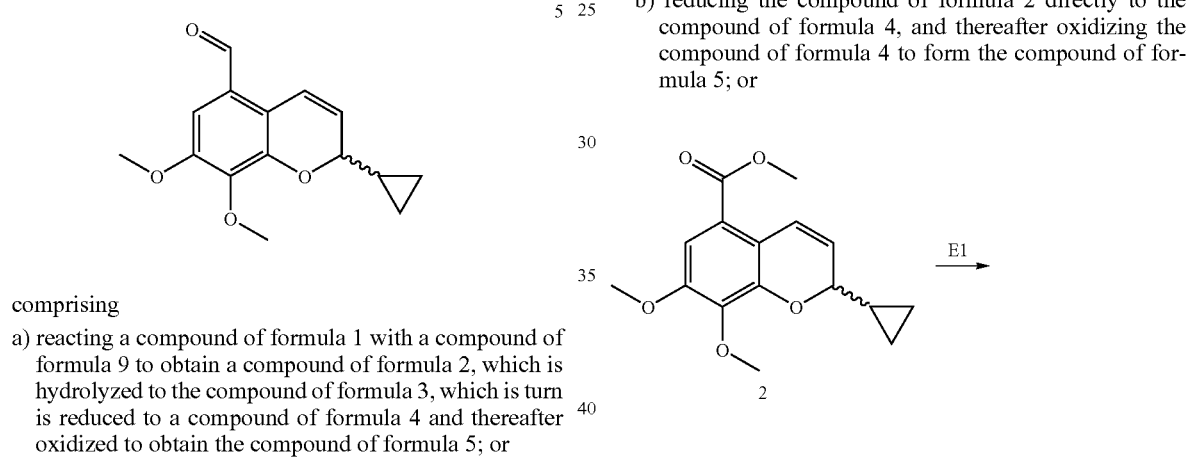

-continued

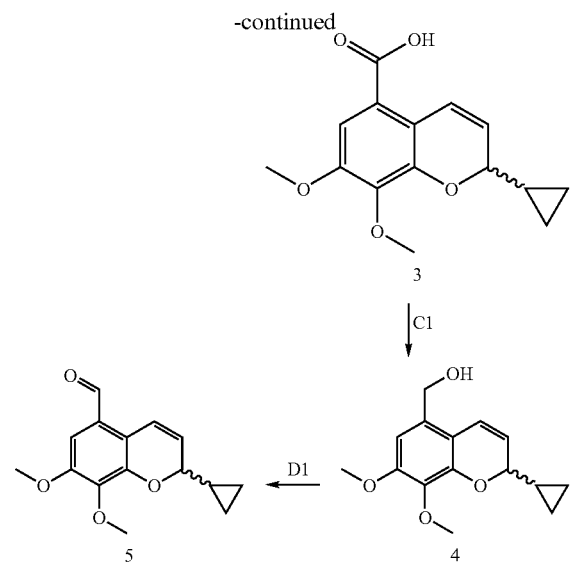

b) reducing the compound of formula 2 directly to the compound of formula 4, and thereafter oxidizing the compound of formula 4 to form the compound of formula 5; or

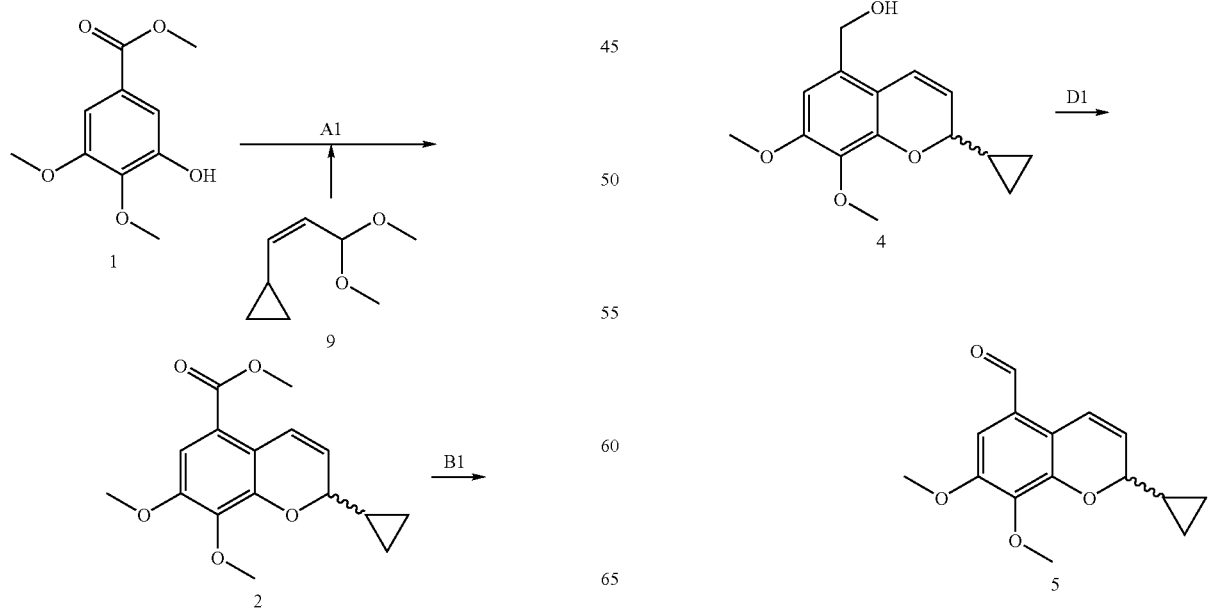

c) reacting a compound of formula 6 with a compound of formula 9 to obtain the compound of formula 5
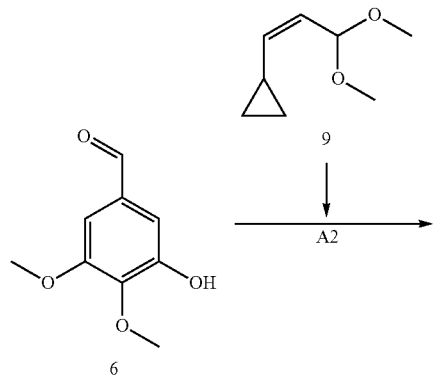
4. The compound of formula 3
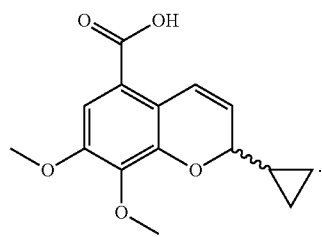
5. The compound of formula 4
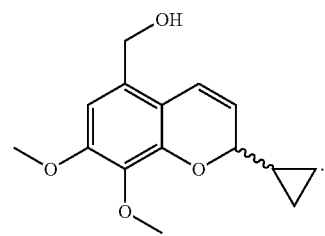
* * * * *